United States Patent
Scott

(10) Patent No.: US 6,799,694 B1
(45) Date of Patent: Oct. 5, 2004

(54) SPECIMAN CUP WITH HANDLE

(76) Inventor: William Scott, 30 Orangewood Dr., Levittown, PA (US) 19057

( * ) Notice: Subject to any disclaimer, the term of this patent is extended or adjusted under 35 U.S.C. 154(b) by 0 days.

(21) Appl. No.: 10/455,966

(22) Filed: Jun. 6, 2003

(51) Int. Cl.[7] ............................................. B65D 25/28
(52) U.S. Cl. ..................................................... 220/763
(58) Field of Search ................................ 220/763, 761, 220/762, 764, 765, 766; 600/573

(56) References Cited

U.S. PATENT DOCUMENTS

| | | |
|---|---|---|
| 3,661,326 A * | 5/1972 | Wilson ........................ 239/60 |
| 3,881,465 A | 5/1975 | Riatto |
| 4,244,920 A | 1/1981 | Manschot et al. |
| D340,768 S | 10/1993 | Jabour |
| D357,066 S | 4/1995 | Jones et al. |
| 5,422,076 A * | 6/1995 | Jones ........................ 422/102 |
| 6,485,438 B1 * | 11/2002 | Minue ........................ 600/573 |

* cited by examiner

Primary Examiner—Stephen Castellano

(57) ABSTRACT

A speciman cup with handle for improving sanitary performance and ease of use of providing a specimen. The speciman cup with handle includes a container member having a bottom wall and a perimeter wall extending upwardly from said bottom wall, the container member defines an interior space, and a lid member couplable to the container member for selectively closing the container.

5 Claims, 2 Drawing Sheets

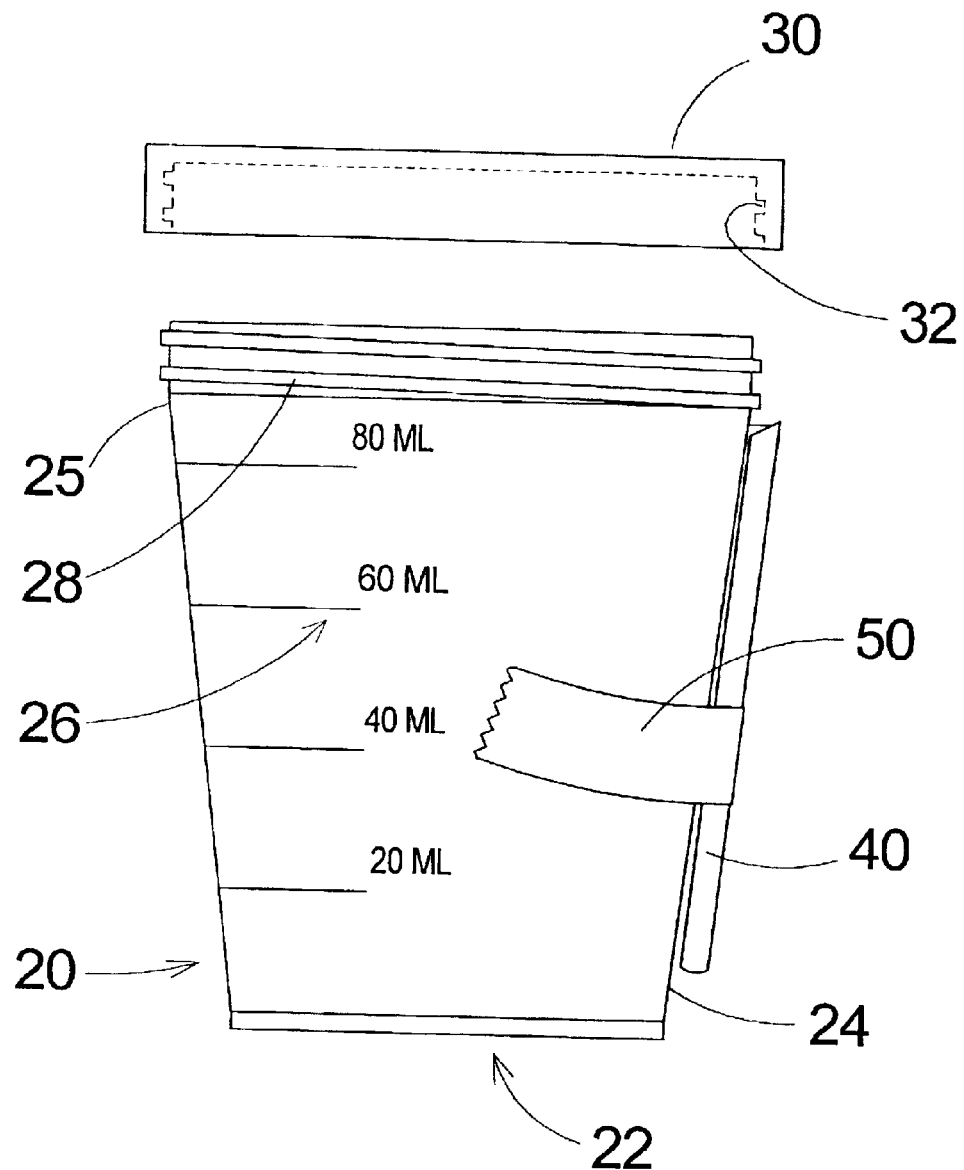

SPECIMAN CUP WITH HANDLE

BACKGROUND OF THE INVENTION

1. Field of the Invention

The present invention relates to specimen cups and more particularly pertains to a new speciman cup with handle for improving sanitary performance and ease of use of providing a specimen.

2. Description of the Prior Art

The use of specimen cups is known in the prior art. More specifically, specimen cups heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,881,465; U.S. Pat. No. 4,244,920; U.S. Patent No. Des. 340,768; and U.S.

While these devices fulfill their respective, particular objectives and requirements, the aforementioned patents do not disclose a new speciman cup with handle. The inventive device includes a container member having a bottom wall and a perimeter wall extending upwardly from said bottom wall, the container member defines an interior space, and a lid member couplable to the container member for selectively closing the container.

In these respects, the speciman cup with handle according to the present invention substantially departs from the conventional concepts and designs of the prior art, and in so doing provides an apparatus primarily developed for the purpose of improving sanitary performance and ease of use of providing a specimen.

SUMMARY OF THE INVENTION

In view of the foregoing disadvantages inherent in the known types of specimen cups now present in the prior art, the present invention provides a new speciman cup with handle construction wherein the same can be utilized for improving sanitary performance and ease of use of providing a specimen.

The general purpose of the present invention, which will be described subsequently in greater detail, is to provide a new speciman cup with handle apparatus and method which has many of the advantages of the specimen cups mentioned heretofore and many novel features that result in a new speciman cup with handle which is not anticipated, rendered obvious, suggested, or even implied by any of the prior art specimen cups, either alone or in any combination thereof.

To attain this, the present invention generally comprises a container member having a bottom wall and a perimeter wall extending upwardly from said bottom wall, the container member defines an interior space, and a lid member couplable to the container member for selectively closing the container.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new speciman cup with handle apparatus and method which has many of the advantages of the specimen cups mentioned heretofore and many novel features that result in a new speciman cup with handle which is not anticipated, rendered obvious, suggested, or even implied by any of the prior art specimen cups, either alone or in any combination thereof.

It is another object of the present invention to provide a new speciman cup with handle which may be easily and efficiently manufactured and marketed.

It is a further object of the present invention to provide a new speciman cup with handle which is of a durable and reliable construction.

An even further object of the present invention is to provide a new speciman cup with handle which is susceptible of a low cost of manufacture with regard to both materials and labor, and which accordingly is then susceptible of low prices of sale to the consuming public, thereby making such speciman cup with handle economically available to the buying public.

Still yet another object of the present invention is to provide a new speciman cup with handle, which provides in the apparatuses and methods of the prior art some of the advantages thereof, while simultaneously overcoming some of the disadvantages normally associated therewith.

Still another object of the present invention is to provide a new speciman cup with handle for improving sanitary performance and ease of use of providing a specimen.

Yet another object of the present invention is to provide a new speciman cup with handle, which includes a container member having a bottom wall and a perimeter wall extending upwardly from said bottom wall, the container member defines an interior space, and a lid member couplable to the container member for selectively closing the container.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a schematic side view of the present invention.

DESCRIPTION OF THE PREFERRED EMBODIMENT

Figure 1:
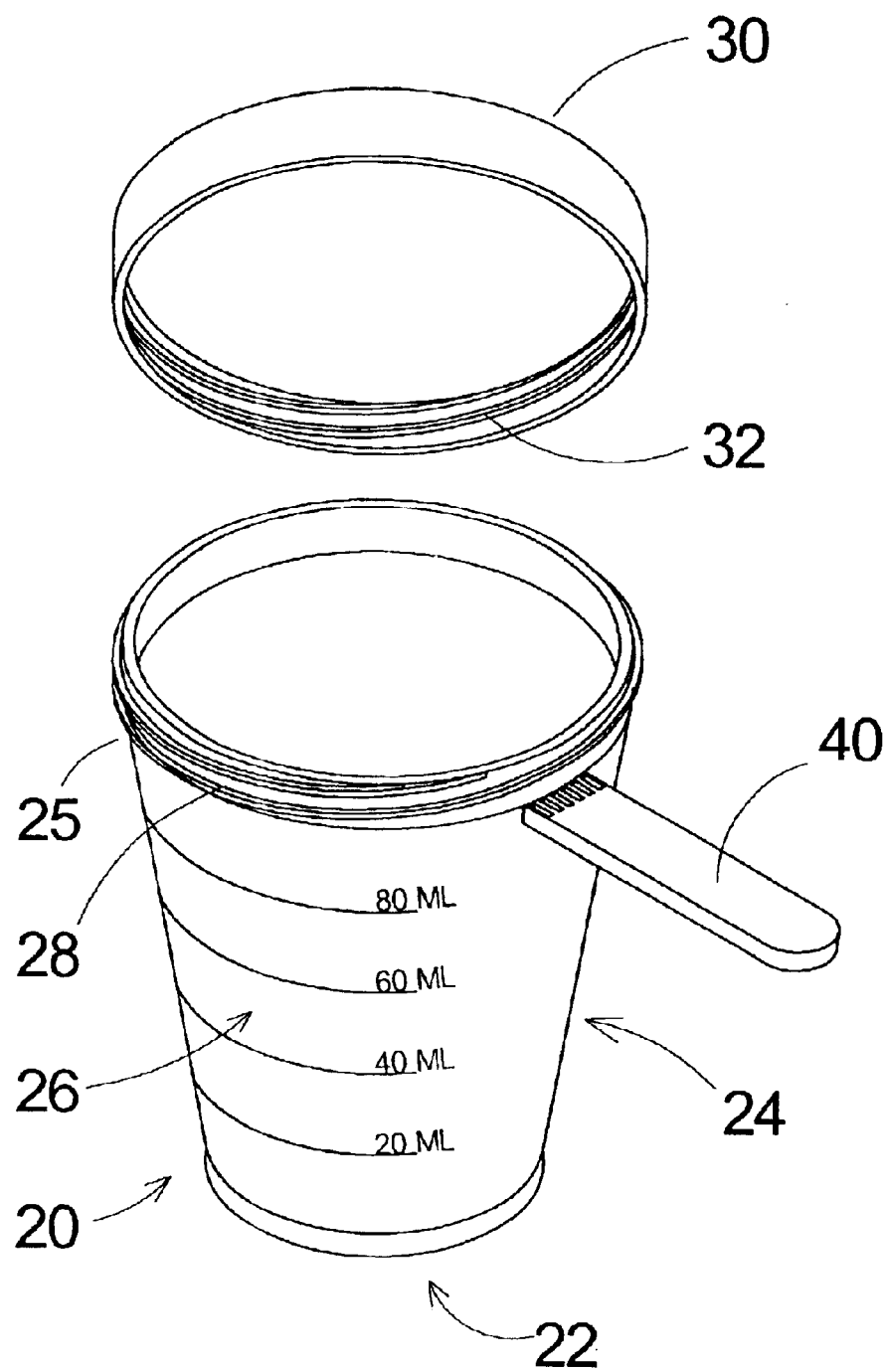
FIG. 1 is a schematic perspective view of a new speciman cup with handle according to the present invention.

With reference now to the drawings, and in particular to FIGS. 1 and 2 thereof, a new speciman cup with handle embodying the principles and concepts of the present invention and generally designated by the reference numeral 10 will be described.

As best illustrated in FIGS. 1 and 2, the speciman cup with handle 10 generally comprises a container member 20 including a bottom wall 22 and a perimeter wall 24 extending upwardly from the bottom wall 22. The container member 20 defines an interior space. The perimeter wall 24 includes an upper end 25 positioned opposite the bottom wall 22. A lid member is couplable 30 to the container member 20 for selectively closing the container 20.

Preferably, the perimeter wall 24 is translucent. Thus a level of contents within the container member 20 is determinable through the perimeter wall 24.

In an embodiment, the perimeter wall 24 further comprises a plurality of indicia 26 indicating a volumetric measurement associate with the level of the contents in the container member 20

In a further embodiment the container member 20 includes threads 28 applied on an exterior surface of the perimeter wall 24 adjacent to the upper end 25. The lid member 30 includes threads 32 applied upon an interior surface. Thus the lid member 30 is threadably couplable to the container member 20.

A handle member 40 may be coupled to the perimeter wall 24 of the container member 20. The handle member 40 facilitates positioning of the container member 20 in a urine stream without the hands of the user coming into contact with the urine stream.

In still a further embodiment, the handle member 40 is hingably coupled to the perimeter wall 24. The handle member 40 has a stored position defined by the handle member 40 being substantially parallel with the perimeter wall 24 and an extended position defined by the handle member 24 being substantially perpendicular to the perimeter wall 24. The handle member 40 is stored to facilitate storage and shipment of the container member 20 in a space efficient manner. The handle member 40 is extended to facilitate positioning of the container member 20 in a urine stream during use.

A securing member 50 may be used for selectively retaining the handle member 40 in the stored position. The securing member 50 preferably comprises single sided adhesive tape positioned across the handle member 40 and abutting the perimeter wall 24.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A specimen collection device comprising:

a container member having a bottom wall and a perimeter wall extending upwardly from said bottom wall, said container member defining an interior space, said perimeter wall having an upper end positioned opposite said bottom wall;

a lid member couplable to said container member for selectively closing said container;

a handle member coupled to said perimeter wall of said container member, said handle member facilitating positioning of said container member in a urine stream without hands of the user coming into contact with the urine stream, said handle member being hingable coupled to said perimeter wall, said handle member having a stored position defined by said handle member being substantially parallel with said perimeter wall, said handle member having an extended position defined by said handle member being substantially perpendicular to said perimeter wall, said handle member being stored to facilitate storage and shipment of said container member in a space efficient manner, said handle member being extended to facilitate positioning of said container member in a urine stream during use; and a securing member for selectively remaining said handle member in said stored position, said securing member comprises single sided adhesive tape positioned across said handle member and abutting said perimeter wall.

2. The device of claim 1, wherein said perimeter wall being translucent such that a level of contents within said container member is determinable through said perimeter wall.

3. The device of claim 2, wherein said perimeter wall further comprises a plurality of indicia indicating a volumetric measurement associate with the level of the contents in said container member.

4. The device of claim 1, wherein said container member having threads applied on an exterior surface of said perimeter wall adjacent to said upper end, said lid having threads applied upon an interior surface whereby said lid being threadably couplable to said container member.

5. A specimen collection device comprising:

a container member having a bottom wall and a perimeter wall extending upwardly from said bottom wall, said container member defining an interior space, said perimeter wall having an upper end positioned opposite said bottom wall;

a lid member couplable to said container member for selectively closing said container;

said perimeter wall being translucent such that a level of contents within said container member is determinable through said perimeter wall;

said perimeter wall further comprises a plurality of indicia indicating a volumetric measurement associate with the level of the contents in said container member;

wherein said container member having threads applied on an exterior surface of said perimeter wall adjacent to said upper end, said lid having threads applied upon an interior surface whereby said lid being threadably couplable to said container member;

a handle member coupled to said perimeter wall of said container member, said handle member facilitating positioning of said container member in a urine stream without hands of the user coming into contact with the urine stream;

wherein said handle member being hingable coupled to said perimeter wall, said handle member having a stored position defined by said handle member being substantially parallel with said perimeter wall, said handle member having an extended position defined by said handle member being substantially perpendicular to said perimeter wall, said handle member being stored to facilitate storage and shipment of said container member in a space efficient manner, said handle member being extended to facilitate positioning of said container member in a urine stream during use;

a securing member for selectively retaining said handle member in said stored position said securing member comprises single sided adhesive tape positioned across said handle member and abutting said perimeter wall.

* * * * *